United States Patent [19]

Hettiarachchi et al.

[11] Patent Number: 5,238,553
[45] Date of Patent: Aug. 24, 1993

[54] REFERENCE ELECTRODE ASSEMBLY AND PROCESS FOR CONSTRUCTING

[75] Inventors: Samson Hettiarachchi, Menlo Park; Herking Song, Fremont, both of Calif.; Digby D. Macdonald, State College, Pa.

[73] Assignee: Electric Power Research Institute, Palo Alto, Calif.

[21] Appl. No.: 881,157

[22] Filed: May 11, 1992

[51] Int. Cl.[5] .......................................... G01M 27/26
[52] U.S. Cl. .................... 204/435; 204/421; 204/422
[58] Field of Search ............... 204/435, 433, 420, 416, 204/419, 431, 422

[56] References Cited

U.S. PATENT DOCUMENTS

| | | | |
|---|---|---|---|
| 3,126,328 | 3/1964 | Hutchison et al. | 204/435 |
| 3,709,813 | 1/1973 | Johnson et al. | 204/420 |
| 4,031,606 | 6/1977 | Szonntagh | 204/420 |
| 4,264,424 | 4/1981 | Niedrack | 204/433 |
| 4,575,410 | 3/1986 | Neti | 204/433 |

OTHER PUBLICATIONS

A Solid Polymer Electrolyte Internal Reference Electrode for High Temperature Aqueous Systems, by S. Hettiarachchi and D. D. Macdonald, J. Electrochem. Soc. 134, May '87, pp. 1307–1308.
Silver-Silver Chloride Thermocells and Thermal Liquid Junction Potentials for Potassium Chloride Solutions at Elevated Temperatures, by D. D. Macdonald, A. C. Scott, P. R. Wentrcek, J. Electrochem. Soc. 126, Sep. 3 79, pp. 1618–1624.
External Reference Electrode for Use in High Temperature Aqueous Systems, by D. D. Macdonald, A. C. Scott, P. R. Wentrcek, J. Electrochem. Soc. 126, Jun. '79, pp. 908–911.

Primary Examiner—John Niebling
Assistant Examiner—Bruce F. Bell
Attorney, Agent, or Firm—Flehr, Hohbach, Test, Albritton & Herbert

[57] ABSTRACT

A reference electrode for use in measuring electrochemical corrosion potential and pH of, for example, water in a drum boiler at supercritical temperatures and which is corrosive includes an alumina or zirconia tube which is packed with a bulk solid electrolyte. The electrolyte consists of a mixture of silver chloride and glass in an optimally 2 to 4 weight ratio or glass particles with silver chloride precipitated around each particle. A solidified silver chloride electrode interfaces with the bulk electrolyte and has embedded in it a conductive silver electrode which provides the electrical contact. Use of the foregoing provides an immobilized solid electrolyte which displays stability and integrity as the temperature and pressure cycles between extremes.

6 Claims, 5 Drawing Sheets

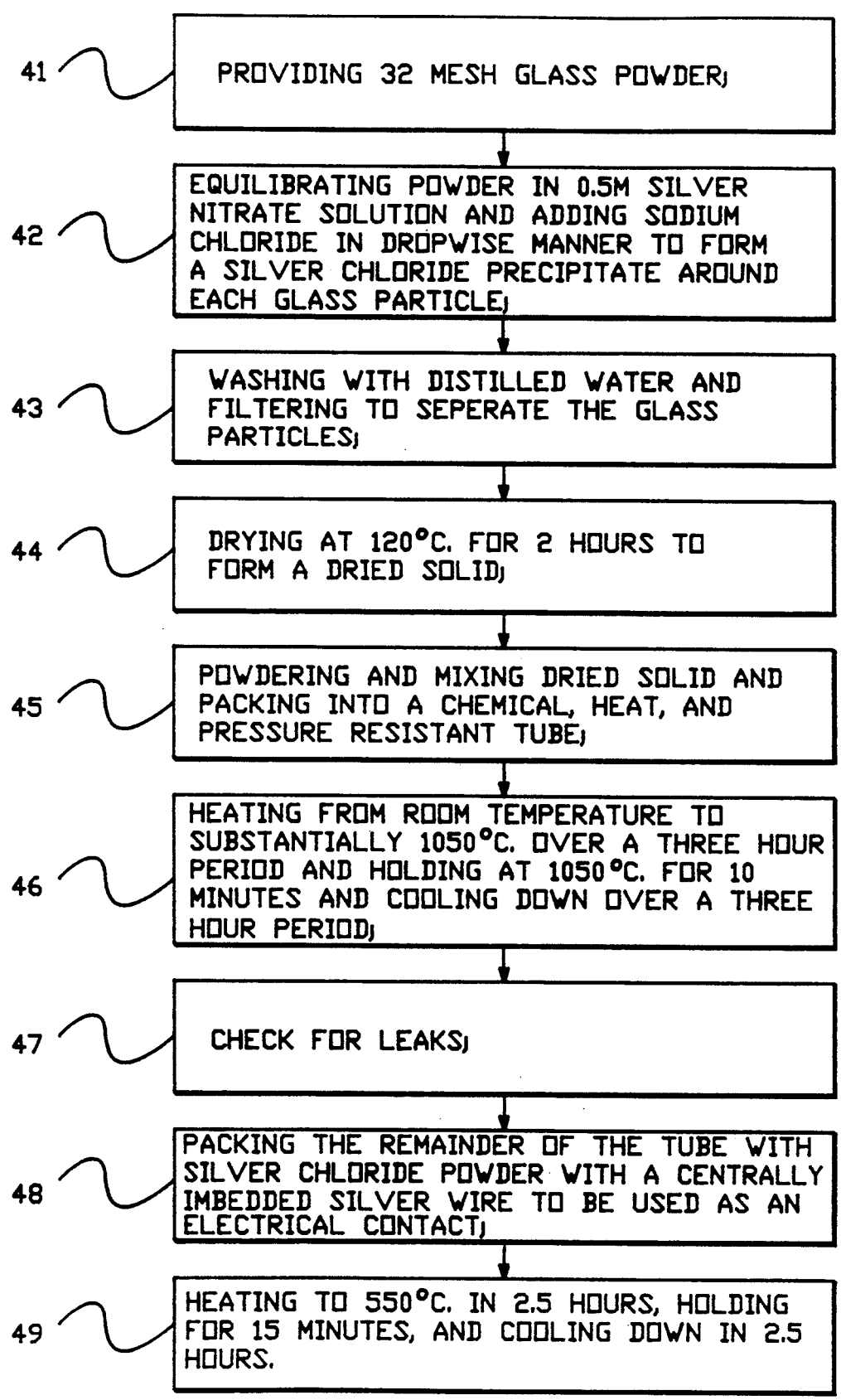
FIG.—5

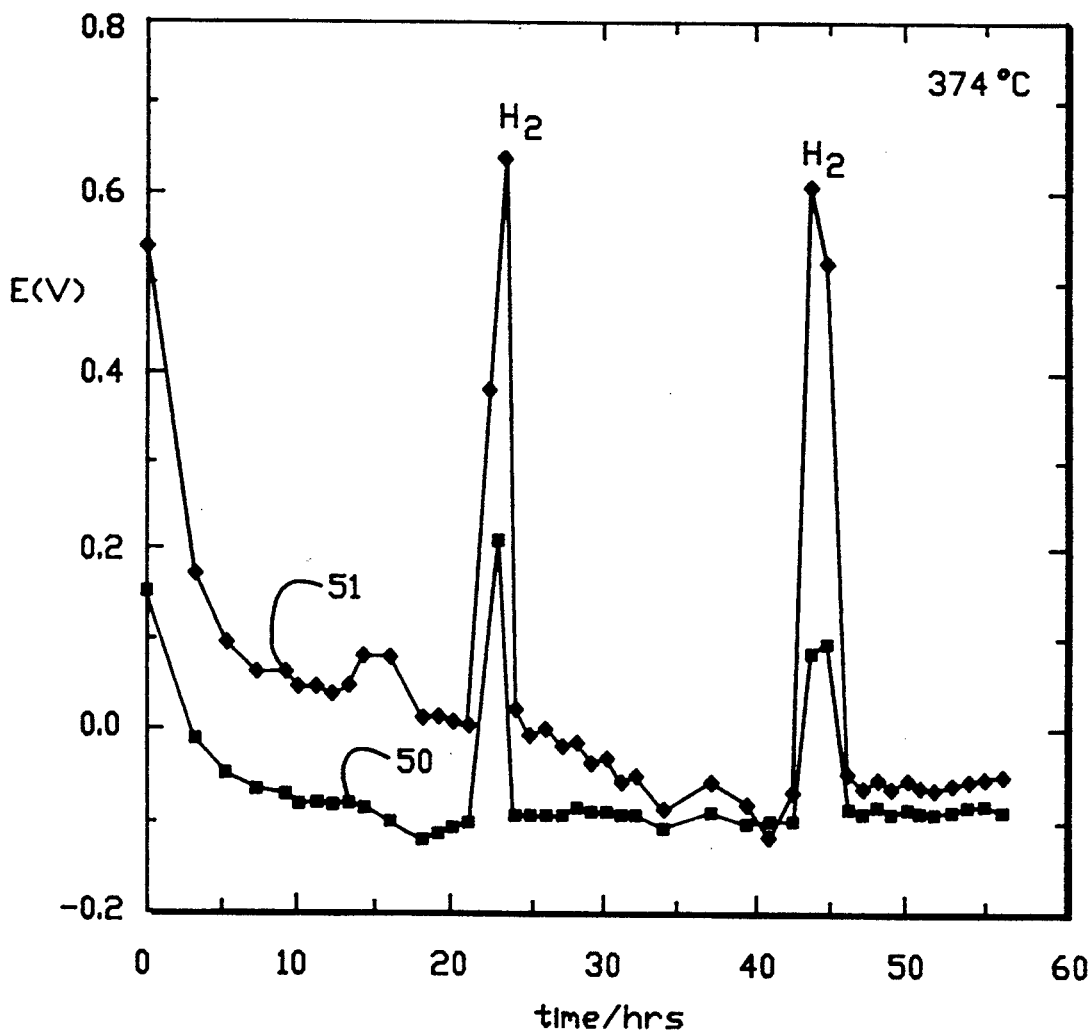
FIG.—6

REFERENCE ELECTRODE ASSEMBLY AND PROCESS FOR CONSTRUCTING

BACKGROUND OF THE INVENTION

The present invention is directed to a reference electrode assembly and a process for construction therefor and specifically a reference electrode useful for operation in aqueous solutions at supercritical temperatures.

In power generating systems such as fossil power plants, the high temperature water used at supercritical temperatures (at or above 374° C.) becomes very corrosive towards metals. To monitor corrosion, two important parameters necessary are electrochemical corrosion potential (ECP) and pH. It is desirable to continually monitor these parameters. However, long term monitoring in fossil plants is only possible by using corrosion reference electrodes and pH sensors that have proved ability to withstand supercritical temperatures over a long period of time. In the past, research has been performed to develop techniques for measuring potential and pH in high temperature aqueous systems. For lower temperature nuclear systems(e.g., 284° C.), a solid polymer electrolyte based Ag/AgCl reference electrode was used in which the solid polymer electrolyte contained a chloride ion. Such an electrode is described in the Journal of Electrochemical Society, Vol. 134, page 1307 (1987), co-authored by S. Hettiarachchi and D. D. Macdonald inventors of the present application) and titled "A Solid Polymer Electrolyte Internal Reference Electrode For High Temperature Aqueous Systems." However, Teflon (a trademark) is used in the construction of this electrode. At temperatures above 320° C., reference electrodes free of Teflon are required. In summary, the existing technologies have had two fundamental limitations; the first is the material stability and the second is lack of integrity as the temperature and pressure cycles between expected extremes.

OBJECT AND SUMMARY OF THE INVENTION

It is therefore an object of the present invention to provide an improved high temperature reference electrode.

In accordance with the above object, a reference electrode assembly comprises a high temperature stable tube resistant to chemicals, pressure and heat. A solid state glass electrolyte doped with silver chloride is packed in the tube at the lower end. The upper end of the tube contains solidified silver chloride which interfaces with the interior end of the solid state glass electrolyte to provide a reversible ion at the interface for a condition of equilibrium. A silver wire for use as an electrical contact is imbedded in the solidified silver chloride. There are means for coupling the other bottom end of the solidified electrolyte to a high temperature corrosive fluid to be monitored using the reference electrode.

Two methods of construction for the above device are also provided.

BRIEF DESCRIPTION OF THE DRAWINGS

FIG. 5 is a flow chart showing the construction of another reference electrode of the present invention.

FIG. 6 illustrates the operating characteristics of the electrode of FIG. 5.

DETAILED DESCRIPTION OF PREFERRED EMBODIMENTS

Figure 1:
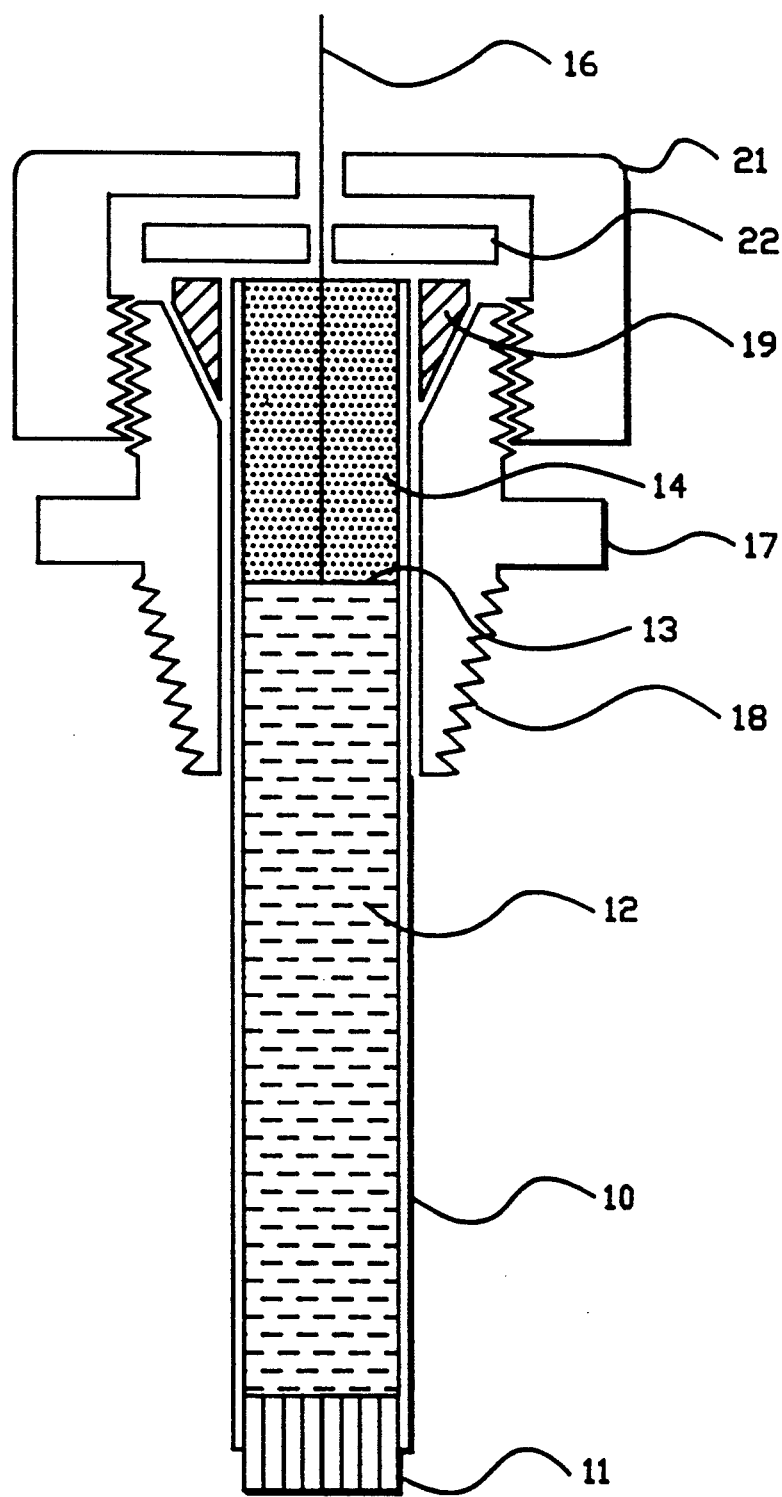
FIG. 1 is a cross sectional view of a reference electrode embodying the present invention.

FIG. 1 illustrates a cross section of the reference electrode where a chemical, heat and pressure resistant alumina (or zirconia) tube 10 would be inserted in the high temperature corrosive fluid such as boiler water in a power plant. The bottom of the tube is blocked by a porous zirconia plug 11. Packed in the lower portion of the tube 10 is a solid state glass electrolyte 12 doped with silver chloride. In one embodiment it is a mixture of glass and silver chloride which has optimally a weight ratio of silver chloride to glass of 2 to 4 but in any case greater than 1 to 4 and less than 3 to 4. At interface 13 there is provided a solidified silver chloride element 14 which interfaces with the bulk electrolyte 12 to provide a reversible ion, namely, chloride, to thus provide a condition of equilibrium for reversibility. A silver wire 16 is embedded in the silver chloride element 14. Alumina (or zirconia) tube 10 is connected to a swagelock fitting 17 which has a tapered thread 18. It is sealed at the upper end by a graphite ferrule 19. Then over the entire top of the structure is placed a lock nut 21 which seals against a steel safety washer 22.

Figure 4:
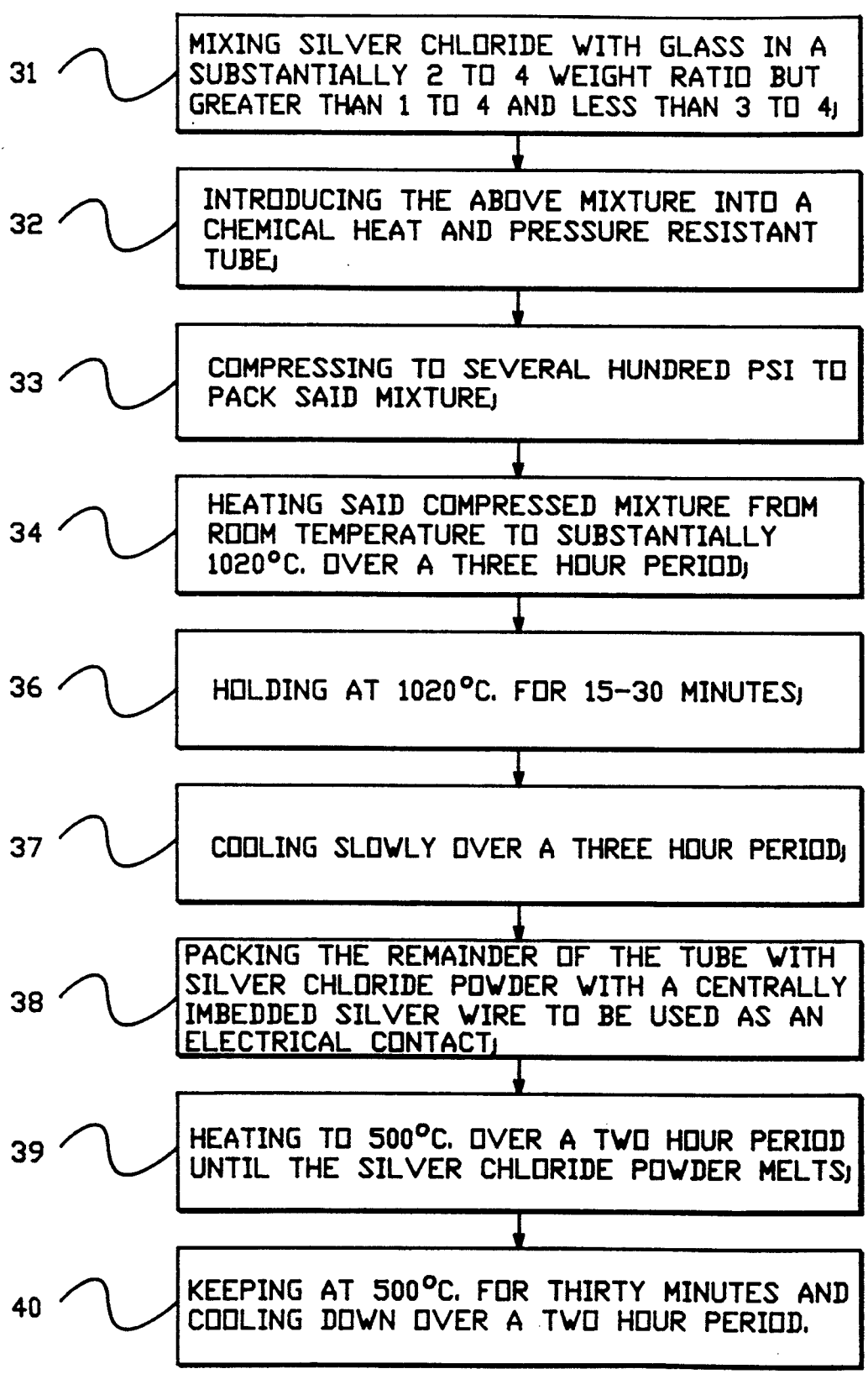
FIG. 4 is a flow chart showing the construction of one reference electrode of the present invention.

One embodiment of the reference electrode of FIG. 1 is constructed by the steps shown in FIG. 4 where in step 31 silver chloride is mixed with glass in a substantially 2 to 4 weight ratio but in any case greater than 1 to 4 but less than 2 to 4. For example, if the weight ratio was 1 to 4, this means there is a large amount of glass present and ionic conductivity is lost in that there are not enough chloride ions in the matrix mixture causing a slowness in response time because of high impedance. On the other hand, a 3 to 4 ratio or above means less glass which may allow leaks due to inadequate binding in the mixture. A 2 to 4 ratio is ideal in that response time and ionic conductivity are adequate. Moreover, the silver chloride is immobilized and meets the objectives of long term stability and integrity in that no leaking or leaching occur. This is to be contrasted with prior liquid systems which could not, of course, exist at supercritical temperatures. Previous proposed solid state systems are not stable enough, and in any case will not maintain system integrity at supercritical temperatures.

Still referring to FIG. 4, in step 32 the mixture is introduced into the tube and in step 33 compressed to several hundred psi to pack the mixture. In step 34 the mixture is heated to a temperature of 1020° C. in 3 hours, held there in step 36 for 15–30 minutes and thereafter cooled slowly in step 37 over a three hour period. Then in step 38, substantially the remainder of the tube shown at 14 in FIG. 1 is packed with silver chloride powder and with the centrally embedded silver wire 16 and in step 39 heated to 500° C. over a two hour period until the silver chloride powder melts. In the last step 40, the melted silver chloride is kept at 500° C. for thirty minutes and then cooled down over a two hour period.

Figure 2:
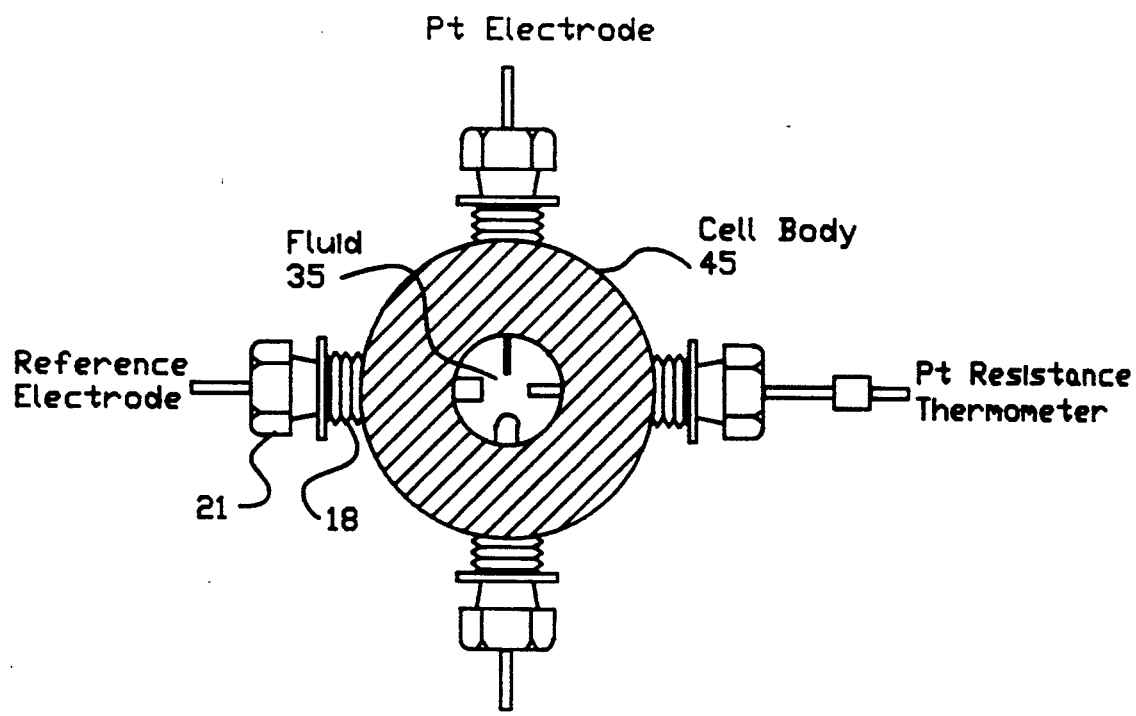
FIG. 2 is a cross sectional view of a test set up for use of the reference electrode in the context of an actual measurement of a high temperature corrosive aqueous medium.

The foregoing was tested in the test set up shown in FIG. 2 where the threaded portion 18 of the reference electrode is screwed into a cell body 45 which contains the fluid 35 which is at a supercritical temperature (greater than 374° C.) having a pH similar to actual conditions. Other probes are a YSZ pH sensor, a platinum electrode and a platinum resistance thermometer as indicated. (YSZ stands for yttria-stabilized zirconia).

Figure 3:
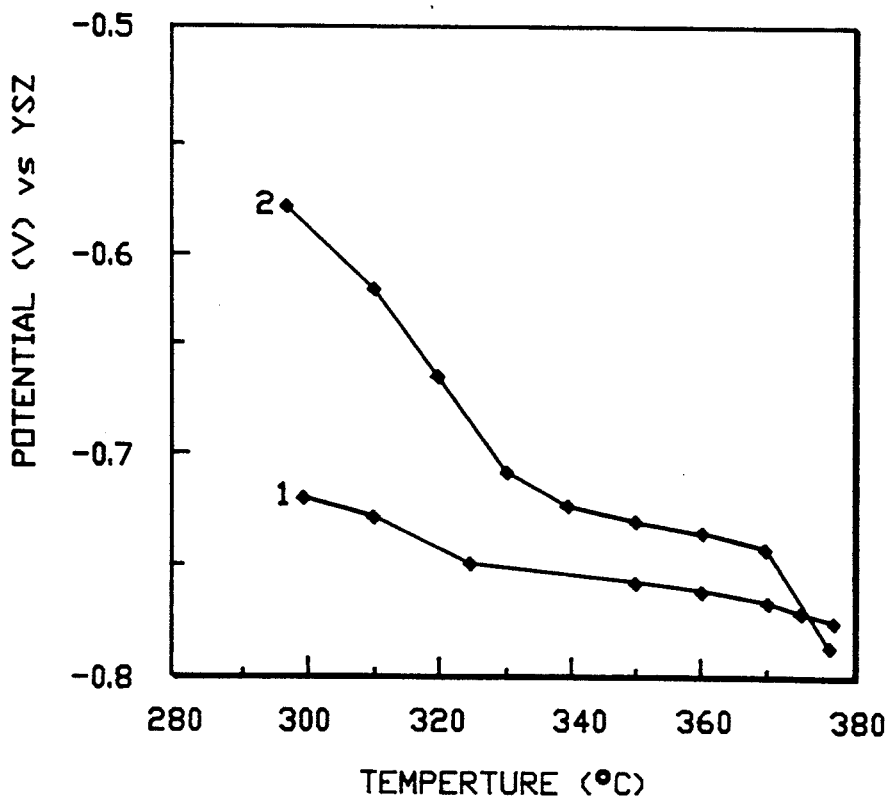
FIG. 3 illustrates the operating characteristics of one reference electrode embodying the present invention.

FIG. 3 shows the performance of two different reference electrodes constructed in accordance with one embodiment of the present invention; specifically a reference electrode of the type in which silver chloride is mixed with glass in a 2 to 4 ratio. Potentials of the reference electrode were measured against the YSZ pH sensor so that when the pH of the solution is changed, only the potential of the YSZ pH sensor changes. If the observed change follows Nernstian behavior, then it can be concluded that the reference electrode behaves as a true reference. (One curve is labeled "1" and the second curve "2"). It is clear from FIG. 3 that at the supercritical temperature both electrodes approach the same potential value of $0.779 \pm 0.02V$ in $10^{-3}$ M HCl at 376° C. with respect to the YSZ electrode.

It is believed that silver chloride, because of its relatively lower melting point, is ideal for mixing with glass, heating and using it as a bulk electrolyte. This is different than silver phosphate which has a much higher melting point. In addition calcium and lithium phosphates were also tried as bulk or solid state electrodes. These showed a lack of stability because presumably the lithium phosphate or calcium dissolved in the high temperature water after several hours. Thus the use of silver chloride as ionic dopant which has a much lower solubility proved to be ideal.

Another type of bulk solid electrolyte 12 of silver chloride and glass may be used in the present invention and is constructed in accordance with the flow chart of FIG. 5. Here as shown in step 41 a 32 mesh glass powder is provided. (This means a glass powder having particle diameters of 80 microns approximately). In step 42 this powder is equilibrated in 0.5M silver nitrate solution. By adding sodium chloride in a dropwise manner, a silver chloride precipitate is formed around each glass particle. And as shown in step 43, this is washed with distilled water and filtered to separate out the glass particles which are then, as shown in step 44, dried at 120° C. for 2 hours to form a dried solid. At step 45 such dried solid is powdered and mixed and packed into the tube 10. In step 46 the packed dried solid is heated at room temperature to substantially 1050° C. over a three hour period and held at this temperature for ten minutes and cooled down over a three hour period. The solid electrolyte filled tube is then checked for leaks (step 47) by pressurizing one end with air while holding the other end in water. The absence of air bubbles indicates the integrity of the electrode.

In step 48 the upper part of the tube or remainder of the tube is packed with silver chloride powder (again 32 mesh) and a silver wire is imbedded or inserted into the powder which acts as the current collector. The entire tube is then heated in step 49 to 550° C. from room temperature in two and a half hours, held there for 15 minutes and then cooled down for two and a half hours.

Since the small glass particles are uniformly coated with the conductive silver chloride, the ionic conductivity of the above bulk electrolyte is very good. At the same time because of the uniform coating of the particles, the bonding is also good to eliminate leakage. And of course because of the use of silver chloride and glass, as in the first embodiment illustrated in FIG. 4, the common chloride ion still provides for reversibility both at the (referring to FIG. 1) interface 13 between the silver chloride element 14 and the solid electrolyte 12. The bottom end of the solid electrolyte is sealed with a porous zirconia plug 11 which provides communication between the electrode and the corrosive fluid. Thus the electrode works very effectively as shown in the characteristic curve of FIG. 6.

Now referring to FIG. 6, where an electrode is constructed with a bulk electrolyte with the silver chloride precipitated around the glass particles, this provides the performance shown in the FIGURE. Here the same test set up of FIG. 2 is utilized. The curve 51 shows the performance of the platinum electrode. The performance of the new electrode is shown by the curve 50 where it shows its performance against a YSZ pH sensor compared with the curve 51. Here the potential is stable at $0.095 \pm 0.010V$ over a fifty hour test period. The platinum electrode responded to the hydrogen ($H_2$) as expected with the electrode of the present invention having only a mild response. This is merely an artifact since in practical use in the field, the hydrogen content dissolved in water is much lower and thus will not show this artifact.

Doping or dopant is not used in the semiconductor sense but more generally as meaning adding something to a substance (including coating the substance) to contribute a desired quality.

In summary, an improved reference electrode for use at supercritical temperatures in aqueous systems has been provided.

What is claimed is:

1. A reference electrode assembly comprising:
   a high temperature tube resistant to chemicals, heat and pressure;
   a solid state glass electrolyte doped with silver chloride packed in said tube at a lower one end thereof;
   a solidified silver chloride element in the upper end of said tube interfacing with an interior end of said solid state glass electrolyte to provide a reversible ion at the interface for a condition of equilibrium;
   a silver wire for use as an electrical contact imbedded in said solidified silver chloride element; and means for coupling the other end of said solid state electrolyte to a high temperature corrosive fluid to be monitored using the reference electrode.

2. A reference electrode as in claim 1 where said solid state glass electrolyte doped with silver chloride is resistant to leaching or leakage at supercritical temperatures but provides sufficient ionic conductivity and response time for effective use as a reference electrode.

3. A reference electrode as in claim 1 which is constructed by providing a chemical, heat and pressure resistant tube; packing a mixture of silver chloride and glass, with the weight ratio of silver chloride to glass being optimally 2 to 4 in said tube by compressing and heating to provide the said solid state glass electrolyte;
   packing the remainder of the tube with silver chloride powder; and heating said powder to solidify it, with said silver wire embedded in it to provide said electrical contact.

4. A reference electrode as in claim 1 where said means for coupling the other end of said solid state electrolyte to said corrosive fluid is a porous zirconia plug.

5. A reference electrode as in claim 1 where said silver chloride doping is in the form of a precipitate around particles of said glass.

6. A reference electrode as in claim 1, which is constructed by providing a chemical, heat and pressure resistant tube; packing a mixture of silver chloride and glass, with the weight ratio of silver chloride to glass being greater than 1 to 4 and less than 3 to 4 in said tube by compressing and heating to provide the said solid state glass electrolyte;

packing the remainder of the said tube with silver chloride powder; and heating said powder to solidify it, with said silver wire embedded in it to provide said electrical contact.

* * * * *